(12) United States Patent
Buckson

(10) Patent No.: US 8,910,332 B2
(45) Date of Patent: Dec. 16, 2014

(54) INFANT ARM SECURING DEVICE

(76) Inventor: Craig Alan Buckson, Cheverly, MD (US)

( * ) Notice: Subject to any disclaimer, the term of this patent is extended or adjusted under 35 U.S.C. 154(b) by 228 days.

(21) Appl. No.: 13/155,174

(22) Filed: Jun. 7, 2011

(65) Prior Publication Data

US 2011/0231998 A1    Sep. 29, 2011

Related U.S. Application Data

(63) Continuation-in-part of application No. 12/871,695, filed on Aug. 30, 2010, now abandoned.

(60) Provisional application No. 61/278,477, filed on Oct. 7, 2009.

(51) Int. Cl.
*A47D 15/00*    (2006.01)

(52) U.S. Cl.
USPC ........................................ 5/655; 5/494; 5/482

(58) Field of Classification Search
USPC ........ 5/494, 413 R, 655, 482, 647; 2/69, 69.5
See application file for complete search history.

(56) References Cited

U.S. PATENT DOCUMENTS

| | | | |
|---|---|---|---|
| 4,611,353 A | | 9/1986 | Als et al. |
| 5,016,650 A | * | 5/1991 | Marlar ........................ 128/878 |
| 5,852,827 A | | 12/1998 | Lear |
| 6,662,390 B1 | | 12/2003 | Berger |
| 6,839,924 B2 | | 1/2005 | Sims |
| 6,868,566 B2 | | 3/2005 | Gatten |
| 6,928,674 B2 | | 8/2005 | Blackburn |
| D513,357 S | | 1/2006 | Allard |
| D518,990 S | | 4/2006 | Brogden et al. |
| 7,076,819 B2 | | 7/2006 | Trani et al. |
| 7,181,789 B2 | | 2/2007 | Gatten |
| 7,246,392 B2 | | 7/2007 | Schmid et al. |
| 7,254,849 B1 | | 8/2007 | Fiebrich |
| 7,774,875 B1 | | 8/2010 | Zeidman |
| 7,954,187 B1 | | 6/2011 | Earnest |
| 2001/0032357 A1 | | 10/2001 | Fuentes et al. |

OTHER PUBLICATIONS

International Search Report in corresponding application PCT/US10/47945 dated Oct. 29, 2010.

* cited by examiner

*Primary Examiner* — Fredrick Conley
(74) *Attorney, Agent, or Firm* — James J. Livingston

(57) ABSTRACT

A method and device for securing arms an infant. The device includes: an elongate piece of material with vertical and horizontal axes; a right wing having a right fastener at a distal right end, the right fastener part disposed along the horizontal axis and on the back side of the material; a left wing having (i) a left fastener part at a distal left end, the left fastener part disposed along the horizontal axis and on the front side of the material; a sleeve attaching component attached on the front side of the material and located at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of the infant.

16 Claims, 10 Drawing Sheets

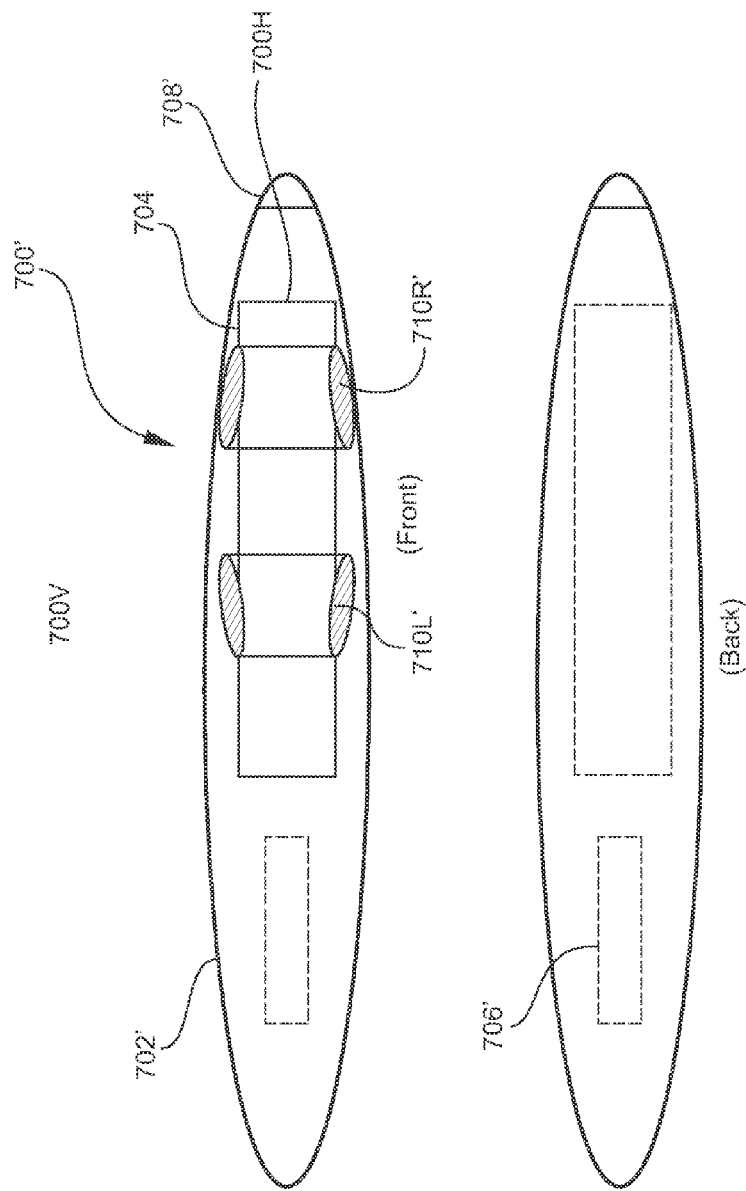

INFANT ARM SECURING DEVICE

CROSS-REFERENCE TO RELATED APPLICATIONS

This application is a continuation in part of U.S. patent application Ser. No. 12/871,695, filed Aug. 30, 2010, which claims the benefit of the U.S. Provisional Patent Application No. 61/278,477, filed Oct. 7, 2009 by the present inventor. Both of these applications are incorporated herein by reference.

TECHNICAL FIELD

Embodiments of the present invention relate to apparatuses used to secure the arms of infants and, more particularly, to accessories that may be used with swaddling cloths, swaddling blankets and the like to secure one or both arms of an infant.

BACKGROUND

The age-old practice of swaddling is a method of wrapping babies in garments of various materials and styles. Studies have shown that the benefits of swaddling include a reduction in sudden infant death syndrome (SIDS) as well as improved sleep habits. Unfortunately, there is a safety concern associated with swaddling. This issue relates to securing an infant's arms in an effective manner to avoid the arms wriggling out of the swaddle. If the infant's arms are not properly secured, there is a risk of the swaddle garment moving upwards towards the infant's face if the infant attempts to free the infant's hands. This is a serious concern, as no swaddle garment should cover an infant's face. In some instances, the infant's arms are simply too strong to hold in its swaddle. In other instances, parents may have difficulty mastering the unique swaddling technique. Many swaddle garments also pose a challenge of holding infant's arms in place due to the lightweight fabric that is often used. All of these issues may be compounded. It is common for parents who experience these challenges to simply abandon swaddling their babies altogether for fear of their child's safety. Therefore there is a need for securing an infant's arms in a fail-safe manner when using a swaddling cloth.

SUMMARY

Technical Problem

The problem is to secure the arms of an infant in a fail-safe manner when used with a swaddling cloth.

Solution to Problem

The swaddling accessory presented herein solves the problem of securing the arms of an infant in a fail-safe manner when used with a swaddling cloth or used to assist a health care provider while examining an infant. In a first embodiment, the swaddling accessory is constructed from a single piece of elongate flexible material such as, but not limited to, a knitted cloth. The elongate flexible material has attached hook and loop fasteners. It is designed and configured so that the infant is placed on the flexible material with the longitudinal axis of the cloth traverse to the infant's torso. Then a first end of the swaddling accessory is placed between the infant's first arm and torso, then over the first arm. Similarly; the second end of the swaddling accessory goes between the infant's second arm and torso, then over the second arm. The two ends of the swaddling accessory are then secured to the back of the elongate flexible material using the hook and loop fasteners. The swaddling accessory secures the infant's arms in a sufficiently snug way so the infant's arms cannot be raised or moved away from the infant's torso. A swaddling cloth may then be put around the infant, over the swaddling accessory, in the usual manner of securing a swaddling cloth to an infant. The swaddling accessory is designed so it adjusts to the infant as the infant grows. It may be manufactured in several sizes to accommodate various sizes of babies. Furthermore, the amount of snugness may be adjusted to determine the amount of movement the infant is allowed. The swaddling accessory may also be used without the swaddling cloth in assisting a health care provider while examining an infant. Additional embodiments are included, including one that allows the swaddling accessory to constrain only one arm of the infant as well as two arms. The swaddling cloth is not part of the invention.

One aspect of the present invention provides a device for securing arms of an infant, comprising: an elongate piece of material having a front side, a back side that is opposite the front side, a vertical axis and a horizontal axis, the axes respectively bisecting the piece of material; a right wing having a right fastener at a right end that is distal from the vertical axis, the right fastener part disposed along the horizontal axis and on the back side; a left wing having (i) a left fastener part at a left end that is distal from the vertical axis, the left fastener part disposed along the horizontal axis and on the front side; and a sleeve attaching component attached on the front side of the elongate piece of material and located at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of the infant. When at least one of the right and left sleeves retains a corresponding arm of the infant, the right and then the left wings are foldable over a chest or a mid-section of the infant and the fasteners cooperate to secure the folded arms in the folded condition.

Another aspect of the present invention provides a device for securing arms of an infant, comprising: an elongate piece of material having a front side, a back side that is opposite the front side, a vertical axis and a horizontal axis, the axes respectively bisecting the piece of material; a right wing having a right fastener at a right end that is distal from the vertical axis, the right fastener part disposed along the horizontal axis and on the front side; a left wing having (i) a left fastener part near a left end that is distal from the vertical axis, the left fastener part disposed along the horizontal axis and on the back side; and a sleeve attaching component attached on the front side of the elongate piece of material along the horizontal, the sleeve attaching component including a pair of sleeves disposed predominantly or entirely on one side of the vertical axis, the pair of sleeves including a right sleeve and a left sleeve, the sleeves disposed and configured to respectively retain right and left arms of the infant. When at least one of the right and left sleeves retains a corresponding arm of the infant, the left and then the right wings are foldable over a chest of the infant and the fasteners cooperate to secure the folded arms in the folded condition.

Still another aspect of the present invention provides a method of securing arms of an infant, comprising: providing an elongate piece of material having a front side, a back side that is opposite the front side, a vertical axis and a horizontal axis, the axes respectively bisecting the piece of material, the elongate piece of material having (i) a right wing having a right fastener at a right end that is distal from the vertical axis, the right fastener part disposed along the horizontal axis and on the back side and (ii) a left fastener part at a left end that is distal from the vertical axis, the left fastener part disposed along the horizontal axis and on the front side; and attaching a sleeve attaching component to the front side of the elongate piece of material and at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of the infant. The right and then the left wings are foldable over a chest or a midsection of the infant and the fasteners cooperate to secure the folded wings in the folded condition.

One aspect of novelty of the present invention is that it is an accessory that works with, but is independent of, most swaddling blankets and cloths. The swaddling accessory secures the infant's arms from being raised or from getting free of the swaddling cloth.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which:

FIGS. 7A-7C respectively illustrate examples of a swaddling device that are consistent with embodiments of the present invention.

DETAILED DESCRIPTION

Figure 1A:
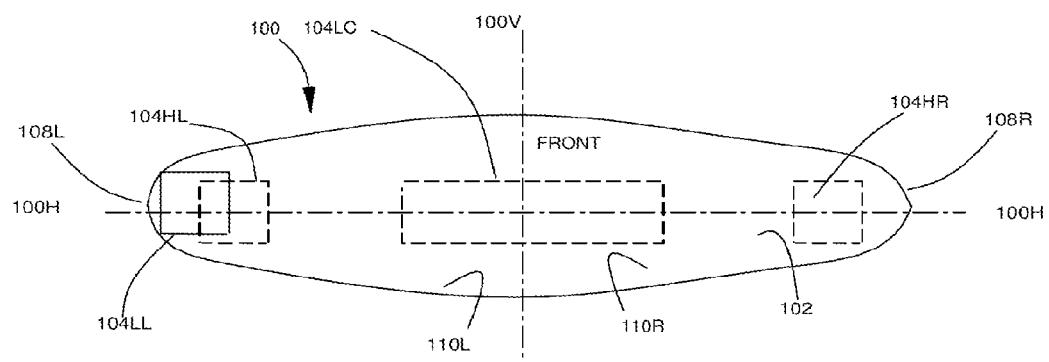
FIG. 1A illustrates a front view of a first embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures.

In this detailed description and the appended claims, terms such as left, right, bottom and top refer to the figure where the reference is first introduced. The exception to the terminology is made when referring to an infant's left arm and right arm; where the usual meaning applies. The term swaddling cloth refers to any blanket, cloth or other garment that is used for swaddling an infant. The terms front and back refer to the front and back of the swaddling accessory when the infant is lying on the swaddling accessory. The term hook component and loop component refer to components of a hook and loop pair of removable attachment means such as, but not limited to VELCRO brand hook and loop fasteners. Two hook and loop pairs may have share a single component. The same numeral is used to refer to a specific item in different figures if it refers to the same physical item, independent of the figure's view. The term flexible material refers to a cloth or other fabric or material suitable for use in swaddling an infant.

Figure 1B:
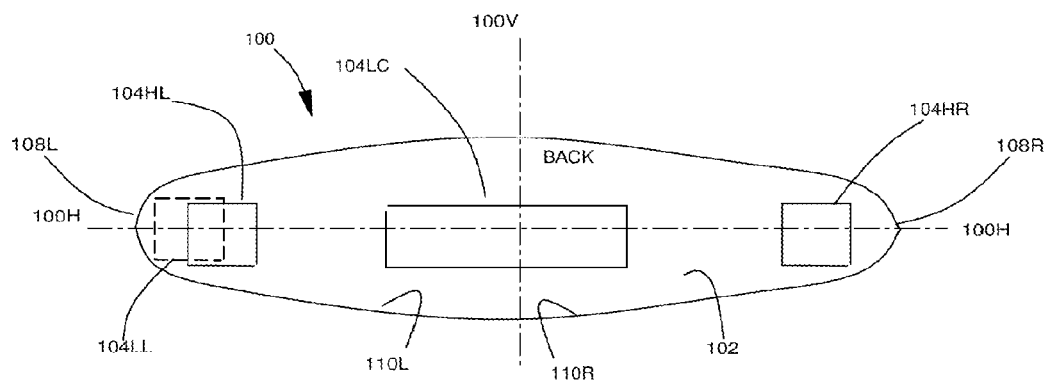
FIG. 1B illustrates a back view of the first embodiment of the present invention.

FIGS. 1A and 1B refer to a first embodiment 100 of the present invention. FIG. 1A illustrates a front view of the first embodiment 100, looking at it from the front while it is positioned on a surface such as a floor or bed. First embodiment 100 is comprised of an elongate piece of an elongate flexible material 102 having a left wing 110L and a right wing 11 OR. The elongate flexible material 102 has one piece of center loop component 104LC and two pieces of hook component, left hook component 104HL and right hook component 104HR attached to the back of the elongate flexible material 102; and one piece of left loop component 104LL attached to the front of the elongate flexible material 102. The center loop component 104LC is positioned on the back of the elongate flexible material 102 centered on the elongate flexible material 102 so it is bisected by the vertical axis 100V. The left loop component 104LL is positioned on the front of the elongate flexible material 102 on the left side towards the left end 108L: the right hook component 104HR is positioned on the front of the elongate flexible material 102 on the right side towards the right end 108R. The left hook component 104HL is positioned on the back of the elongate flexible material 102 on the left side towards the left end 108L. All the hook and loop components, center loop component 104LC, left hook component, 104HL, right hook component 104HR, and left loop component 104LL are positioned centered on the horizontal axis 100H located midway between the top and bottom of the elongate flexible material 102.

Figure 2A:
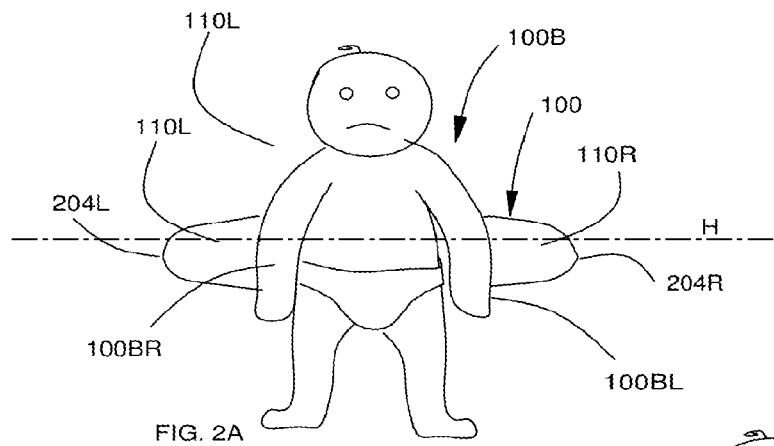
FIG. 2A illustrates a front view of a first step of putting the first embodiment of the present invention on an infant.
Figure 2B:
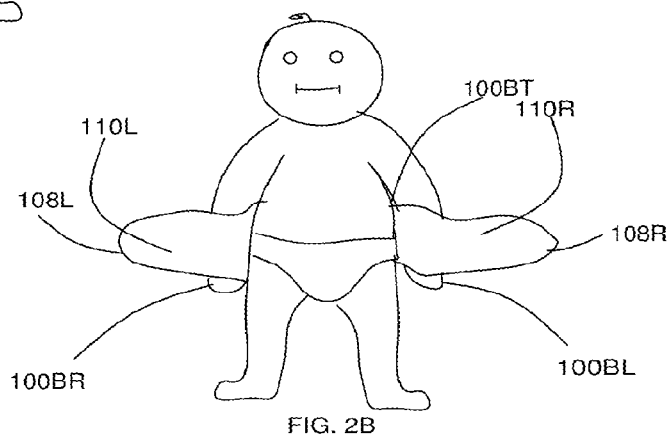
FIG. 2B illustrates a front view of a second step of putting the first embodiment of the present invention on an infant.
Figure 2C:
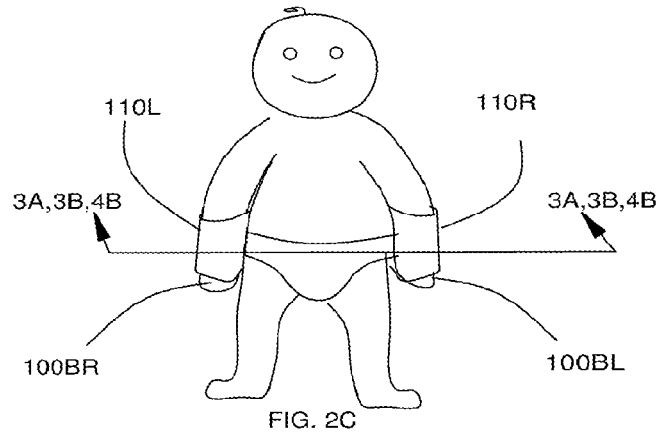
FIG. 2C illustrates a front view of the first embodiment of the present invention when secured on an infant.
Figure 3A:
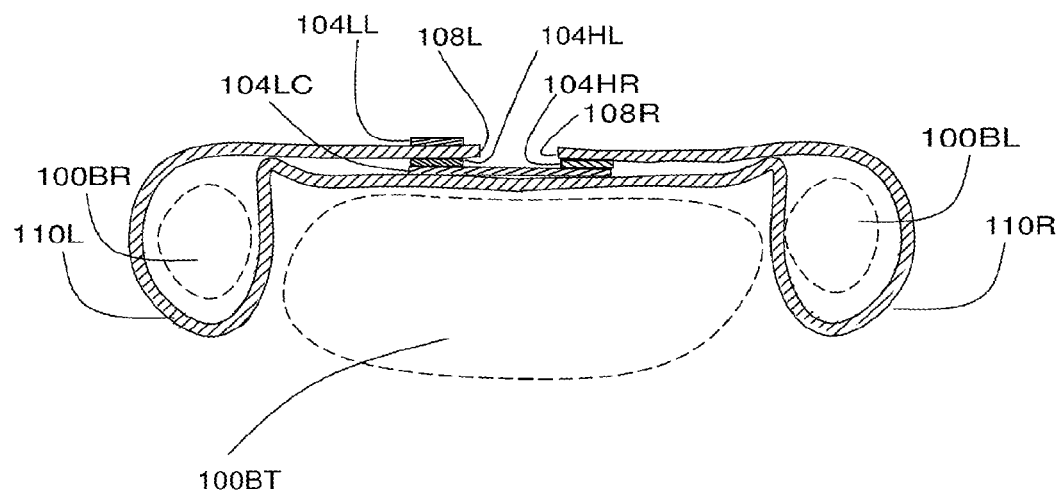
FIG. 3A illustrates a cross section of FIG. 2C when the first embodiment secures the arms of a moderately sized infant.
Figure 3B:
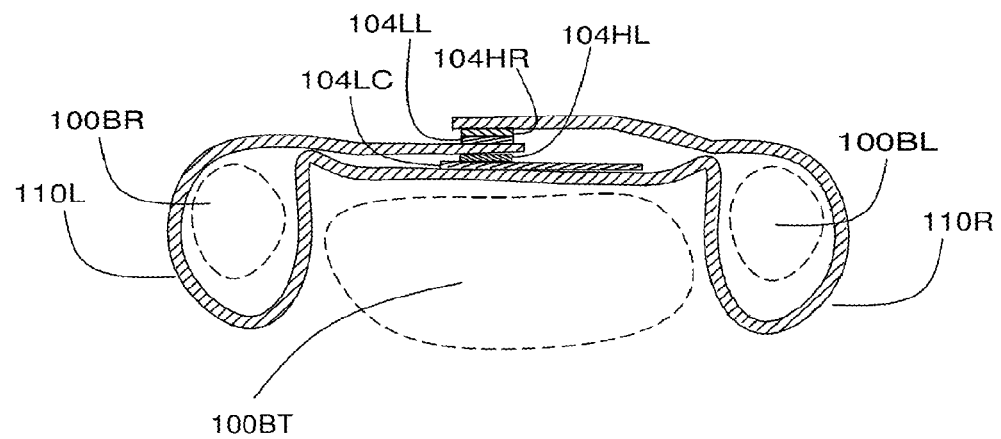
FIG. 3B illustrates a cross section of FIG. 2C when the first embodiment secures the arms of a small infant.

FIG. 1B shows the back of first embodiment 100. The same numerals used in FIG. 1A apply to FIG. 1B. FIGS. 2A through 2C illustrate an overview of the steps involved in wrapping the first embodiment of the present invention on an infant while FIGS. 3A and 3B give a cross section view of first embodiment 100 when wrapped on a moderately sized infant and a small infant respectively. Referring to FIG. 2A, the first step is to place the elongate flexible material 102 on a flat horizontal surface such as a floor or a bed with the front of the elongate flexible material 102 facing upward and the cloth extended with the horizontal axis 100H going from left to right. The infant 100B is then placed on elongate flexible material 102 facing front with the infant's back lying on elongate flexible material 102. The infant is positioned so the bottom edge of the elongate flexible material 102 is just above the infant's wrist and the infant is centered on the elongate flexible material 102.

FIG. 2B shows the second step. The left wing 110L of elongate flexible material 102 is placed between the torso 100BT of the infant and the right arm 100BR and then extended over the right arm 100BR toward the left. The right wing 11 OR of elongate flexible material 102 is placed between the torso 100BT of the infant and left arm 100BL, then extended over the left arm 100BL, and extended to the right.

The third step, also discussed later with reference to FIGS. 3A and 3B, is performed as follows: The left wing 110L is then placed to the back of elongate flexible material 102; the right wing 11 OR is then placed to the back of elongate flexible material 102; and the two wings 110R and 110L are secured to the back of elongate flexible material 102 so that that the left arm 102BL and right arm 102BR are secured snugly.

FIG. 2C illustrates a front view of first embodiment 100 when wrapped on the infant with the arms snugly secured at the sides of the torso 100BT. The specific details illustrating how first embodiment 100 secures the infant's arms are illustrated in the cross section views of FIGS. 3A and 3B.

FIGS. 3A and 3B show two methods for securing first embodiment 100 on the infant. Both FIGS. 3A and 3B are cross section of FIG. 2C. FIG. 3A illustrates how first embodiment 100 is wrapped on a moderate sized infant while FIG. 3B shows how first embodiment 100 is wrapped on a small infant. Refer now to FIG. 3A. With the infant's back lying on the front side of first embodiment 100, the left wing 110L of first embodiment 100 is threaded between the right arm 100BR of the infant and torso 100BT, then around the front of the right arm 100BR of the infant and then under the infant. The left end 108L is then pulled firmly to the right under the infant's back so the right arm 100BR of the infant is held snugly. The left hook component 104HL is then attached to the left side of the center loop component 104LC. This secures the infant's right arm.

The left arm 100BL of the infant is secured similarly. The right wing 110R of first embodiment 100 is threaded between the left arm 100BL of the infant and torso 100BT, then around the front of the left arm 100BL of the infant and then under the infant. The right end 108R is pulled firmly to the left under the infant's back so the left arm 100BL of the infant is held snugly. The right hook component 10411R is then attached to the right side of the center loop component 104LC. This secures the infant's left arm.

FIG. 3B illustrates how first embodiment 100 is attached to an infant that is smaller then the infant illustrated in FIG. 3A. The left wing 110L of first embodiment 100 is wrapped around the infant's right arm in the same manner as described for FIG. 3A. The right wing of first embodiment 100 is also wrapped around the infant's left arm as described for FIG. 3A, but with one difference. The right hook component 104HR is attached to the left loop component 104LL. This secures both of the infant's arms. It is therefore seen that first embodiment 100 can accommodate the infant as she grows in size. FIG. 3B accommodates a small infant while FIG. 3A accommodates a larger infant.

Figure 4A:
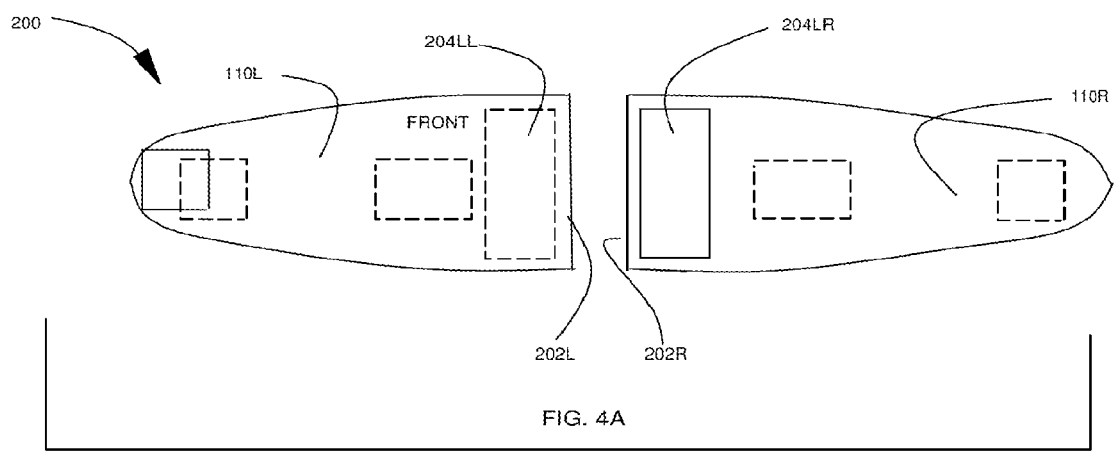
FIG. 4A illustrates a second embodiment of the present invention made from two sections of elongate flexible material.
Figure 4B:
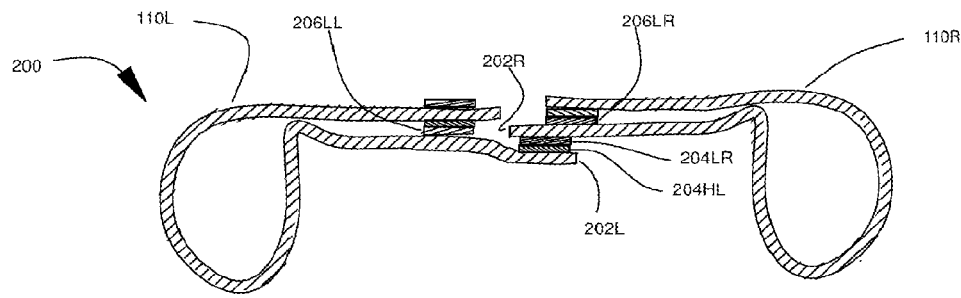
FIG. 4B illustrates a cross section of FIG. 2C for the second embodiment of the present invention.

FIGS. 4A and 4B illustrate a second embodiment 200 of the present invention. FIG. 4A has the same design as FIG. 1A with the following wing differences. Second embodiment 200 is divided into two wings vertically, separating them into approximately two halves, a left wing 110L and a right wing 11 OR. The left wing 110L has a left side hook component 204HL attached to the back near the edge 202L; and the right wing 110S has right side loop component 204LR attached to the front of the right wing 110R near the edge 202R. The center loop component 104LC of first embodiment 100 is replaced by two loop components 206LL and 206LR.

FIG. 4B is a cross section of second embodiment 200 as illustrated in FIG. 2C. The left wing 110L and right wing 11 OR are joined with the right side hook component 204HR attached to the left side loop component 204LL. Once these two wings are attached, securing the infant with embodiment two is done in the same manner as embodiment one. The primary advantage of embodiment two is that after the appropriate sizing is done once, the two wings can stay attached and both arms can easily be secured in subsequent uses of this embodiment without having to reach behind and/or around the infant as compared to the first embodiment.

Figure 5A:
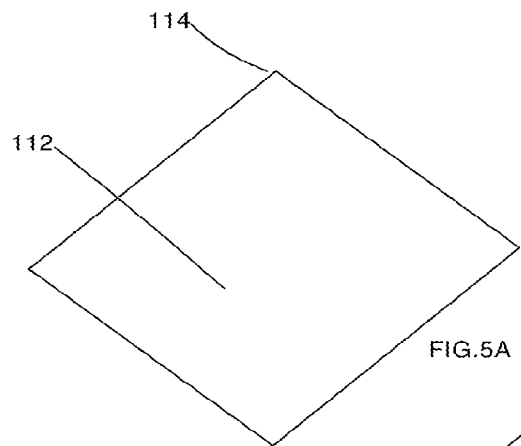
FIG. 5A illustrates a front view of preparing to put on a swaddling cloth positioned diagonally on a flat horizontal prior to application of the first embodiment of the present invention is secured on an infant.
Figure 5B:
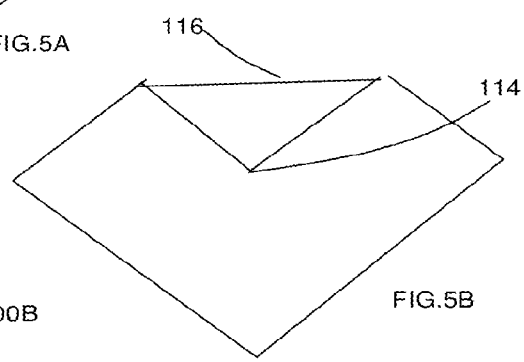
FIG. 5B illustrates a front view of the swaddling cloth with a top corner of the swaddle folded down prior to application of the first embodiment of the present invention being secured on an infant.
Figure 5C:
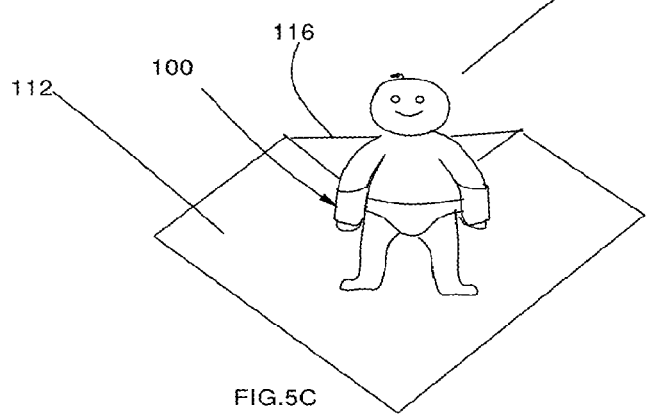
FIG. 5C illustrates a front view of the swaddling cloth wrapped on an infant after the first embodiment of the present invention is secured on an infant.
Figure 5D:
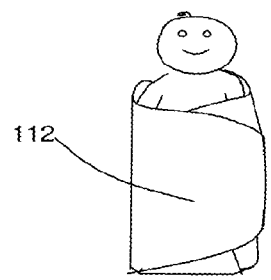
FIG. 5D illustrates a front view of the swaddling cloth wrapped on an infant after the first embodiment of the present invention is secured on an infant.

FIGS. 5A through 5D illustrate the use of first embodiment 100 together with an infant blanket 112 used as a swaddling cloth. FIG. 5A indicated first embodiment 100, positioned diagonally on a flat horizontal surface. FIG. 5B indicates the top corner 114 of the infant blanket folded down. FIG. 5C indicated laying the infant 100B on the infant blanket 112, the top crease 116 of the blanket level with the infant's neck, with first embodiment 100 already secured on the infant. FIG. 5D indicates the infant blanket 112 wrapped around the infant 100B, the wrapping done in the usual manner.

Figure 6A:
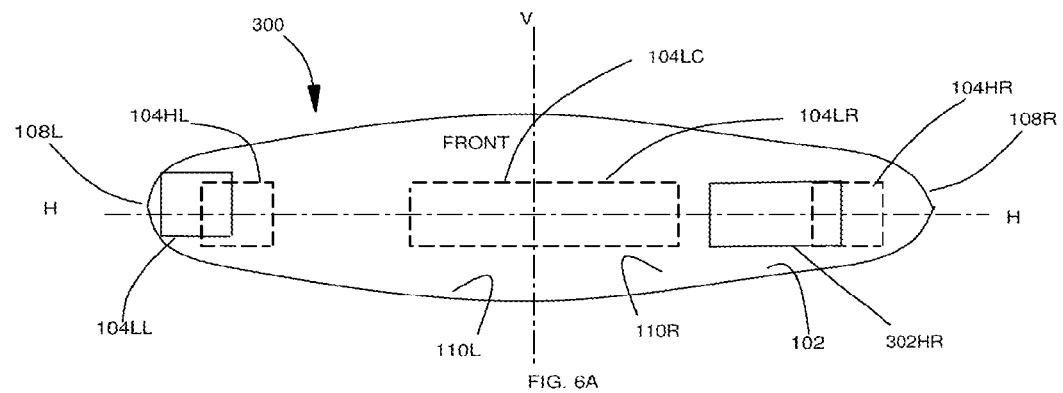
FIG. 6A illustrates a front view of a third embodiment of the present invention designed to secure either one or two arms of an infant.
Figure 6B:
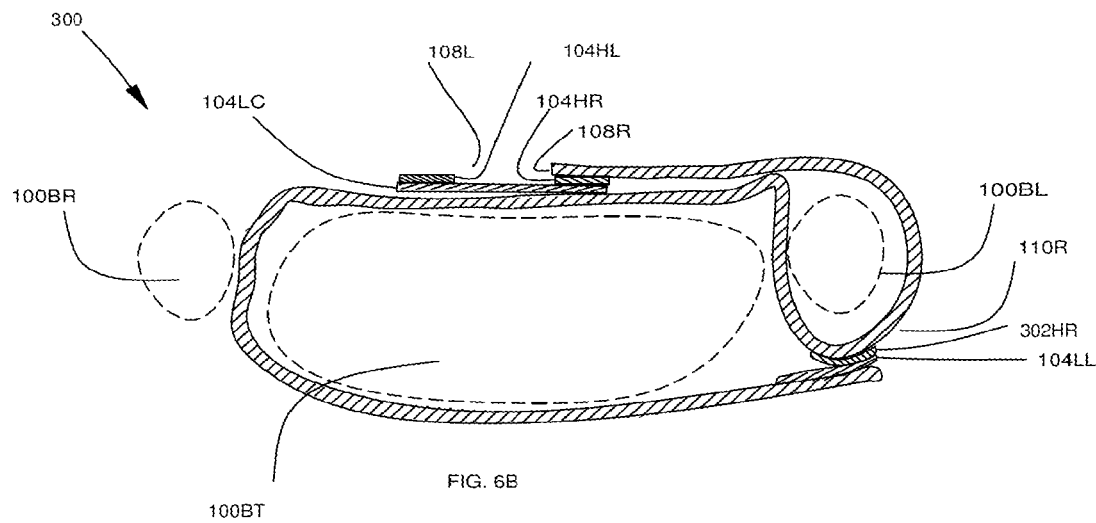
FIG. 6B illustrates a sectional view of the third embodiment of the present invention.
Figure 6C:
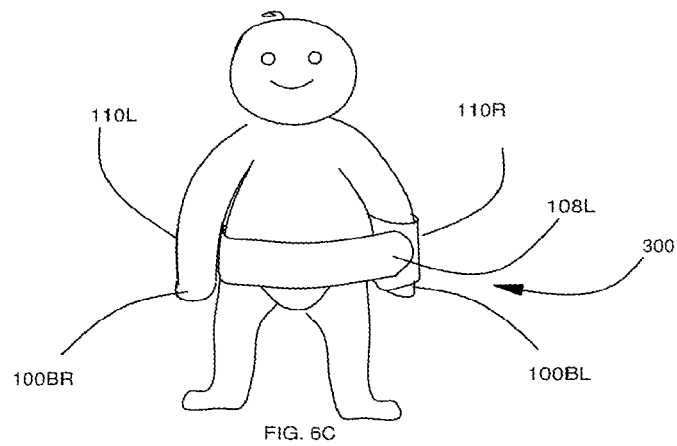
FIG. 6C illustrates a front view of the third embodiment of the present invention securing one arm of an infant.

FIGS. 6A through 6C illustrate a third embodiment 300 of the present invention. Referring to FIG. 6A, third embodiment 300 modifies first embodiment 100 by having a piece of additional right hook component 302HR positioned on the right side of the front of first embodiment 100. Third embodiment 300 permits the swaddling cloth to be used in the same way as first embodiment 100. However, it also allows third embodiment 300 to be used as a one-arm swaddling cloth.

FIG. 6B illustrates a sectional view of third embodiment 300 as it is used as a swaddling accessory securing only one arm. Third embodiment 300 swaddles an infant torso BT and left arm 100BL of infant while keeping the right arm 100BR free. FIG. 6C illustrates third embodiment 300 as used with an infant. As illustrated in FIG. 6B, additional right hook component 302HR engages left loop component 104LL in a manner that keeps left arm 100BL of the infant free. The location and configuration of the components of third embodiment 300 are determined so that third embodiment 300 functions as indicated.

The one arm swaddle of third embodiment 300 assists parents with weaning their infant off the swaddle blanket. One-arm swaddling is a fairly typical approach to this transition. The challenge with this is similar to the challenge with swaddling in general; babies often work their way out of them. Parents are highly motivated to keep their infant's arms secured for as long as they can because of the "startle-reflex" which is a known term to depict the infant's inability to control their arms from moving around while they sleep which often wakes them up. Therefore many want to swaddle as long as is practical and when they are ready to transition out of swaddling, they often attempt to do this one arm at a time. Third embodiment 300 will assist with this. [0037] The three embodiments are dimensioned and configured so they functions as described. The actual dimensions of the swaddling accessory are a design option. Typical dimensions for the first embodiment are 15 cm (6 in) height and 70 cm (23.5) length; however, these dimensions can vary, depending on the size of the infant using the swaddling accessory. The shape of the swaddling accessory can also vary as long as it functions as described herein. Other removable attaching mechanisms may be used instead of the hook and loop means such as buckles or snaps. A knitted fabric of the swaddling accessory works well when also used as the material for a companion swaddling cloth; however, other fabrics may also be used. Several different sizes of swaddling accessories may be used to accommodate the infant from birth until a swaddling accessory is no longer used. The swaddling accessory can also be used in certain situations without a swaddling cloth; for example in a doctor's office to secure the infant's arms during an exam. The elongate flexible material may be made from on or more pieces of material that are attached together by attachment means such as gluing, or stitching.

Figure 7A:
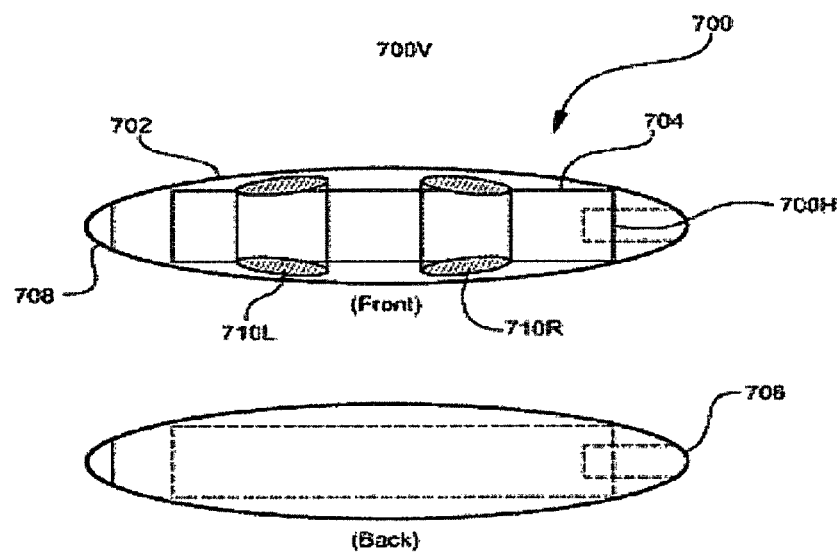

Referring now to FIG. 7A, there is illustrated an example of a device 700 for securing arms of an infant, consistent with an embodiment of the present invention.

The device 700 includes an elongate piece of fabric 702, a sleeve attachment component 704, fasteners 706 and 708, and sleeves 710L and 710R.

The elongate piece of material 702 may be in the shape of an ellipse, as illustrated. However, it is to be understood that other shapes are both possible and contemplated. As illustrated, the elongate piece of material 702 has intersecting vertical and horizontal axes (700V and 700H). The vertical axis 700V defines respective right and left sides of the elongate piece of material 702 and divide the elongate piece of material 702 into respective left and right wings.

The elongate piece of material 702 includes, at a distal right side and on the back side, a first fastener part 706. As will be explained in detail below, the first fastener part 706 cooperates with another fastener part (708) to retain the wings in a folded condition. The first fastener part 706 is disposed along the horizontal axis 700H.

The elongate piece of material 702 also includes, at a distal left side and on the front side, a second fastener part 708. The second fastener part 708 is disposed along the horizontal axis 700H.

As stated above, the fastener parts cooperate to retain the wings in a folded position. To this end, each fastening part may be of a loop or a hook configuration, to yield a hook and loop fastener system, such as VELCRO®.

The sleeve attachment component 704 includes two sleeves 710L and 710R and attaches sleeves 710L and 710R to the elongate piece of fabric 702. To this end, the sleeve attachment component 704 is attached to the front side of the elongate piece of material 702. Further, the sleeve attachment component 702 may be removable attached to the elongate piece of fabric 702.

Figure 7C:
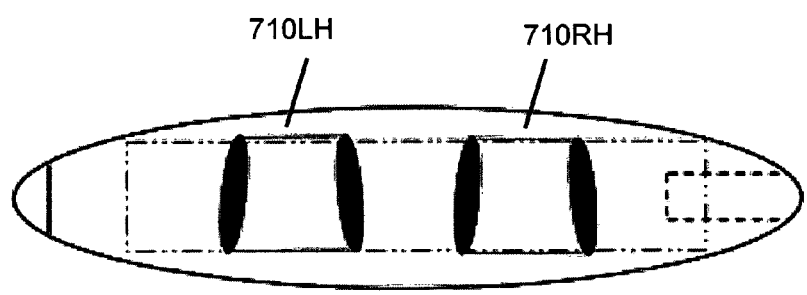

The sleeve attachment component 704 is illustrated as rectangular in shape. It is to be understood, however, that other shapes are both possible and contemplated. Also, the sleeve attachment component 704 is located at the intersection of the axes, as illustrated in FIG. 7. It is to be understood, however, that other configurations are both possible and contemplated.

The sleeves 710 are each adapted and configured to accept and removably retain an infant's arm. As illustrated in FIG. 7, the sleeves 710 may be vertically oriented and disposed in parallel to the vertical axis. However, other orientations are both possible and contemplated. By way of non-limiting example, the sleeves 710LH and 710RH maybe horizontally oriented and disposed along the horizontal axis 700H. Still further, the sleeves need not share the same orientation. For example, each sleeve may be tilted relative to vertical or horizontal. Non-limiting examples of this titling include tilts inward and outward.

Optionally, the sleeves 710 may be removably attached to the sleeve attachment component 704 in an entirely removable, partially removable, and/or adjustably removable manner. Also, optionally, the sleeves 710 may be one continuous material or may open and close via a flap method.

In operation, an infant's right and left arms are inserted into the respective right and left sleeves 710. Then, the right wing is folded over the infant's chest. Thereafter, the left wing is folded over the right wing. In this folded condition, the fastener parts 706 and 708 come into contact and removably fasten (or bind) the wings. In this way, the device provides two levels of arm security. First, the sleeves 710 each retain an arm. Second, the wings retain the arms. Advantageously, because of this two layer arm security, only one of the infant's arms needs to be inserted and retained in a sleeve 710 to adequately swaddle an infant when one arm swaddling/securing is desired. Here, when one arm swaddling/retention is desired, the right and then the left wings are foldable over a chest or a mid section of the infant and the fasteners cooperate to secure the folded or straightened arms in the folded or straightened condition.

Referring now to FIG. 7B, there is illustrated an alternative example of a device 700' for securing arms of an infant, consistent with an embodiment of the present invention.

The device 700' is similar in construction to the device 700 of FIG. 7A in most respects. The device 700' differs from the device 700 in that the sleeve attachment component 704' is disposed so that the sleeves 710 are disposed predominantly or entirely on one side of the vertical axis 700V', as illustrated in FIG. 7B. In this alternative configuration, the elongate piece of fabric 702' is of a greater eccentricity than that of elongate piece of fabric 702 of FIG. 7. The increased eccentricity, coupled with the offset positioning of the sleeves, permits the left wing to be folded first, to still cover the sleeves 710, and to be tucked behind an infant's back so that it between the right sleeve and the infant's back. Further, to facilitate the cooperation of the fasteners 706' and 708', the right fastening component is disposed on the front side of the elongate piece of fabric 702' while the left fastening component 708' is located on the back side.

Figure 8:
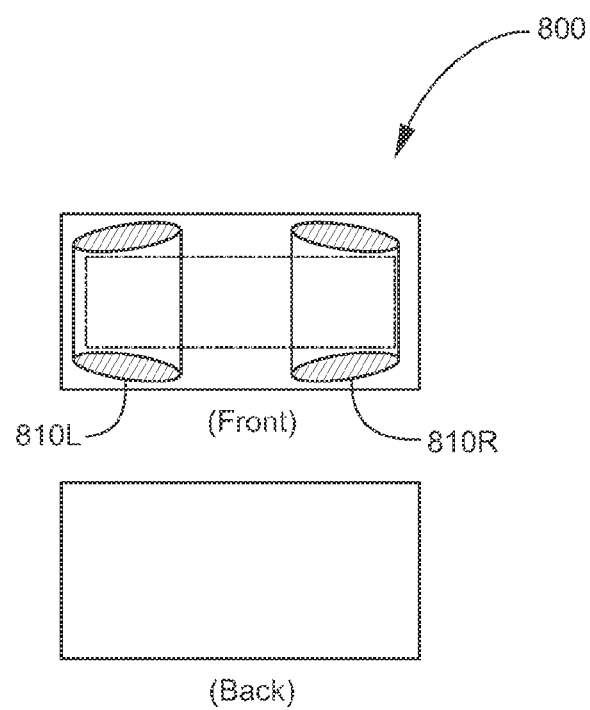
FIG. 8 illustrates another example of a swaddling device that is consistent with an embodiment of the present invention.

Referring to FIG. 8, illustrating the optional nature of the elongate piece of fabric (702 of FIG. 7A or 702' of FIG. 7B) the device may do away with the elongate piece of fabric.

Figure 9:
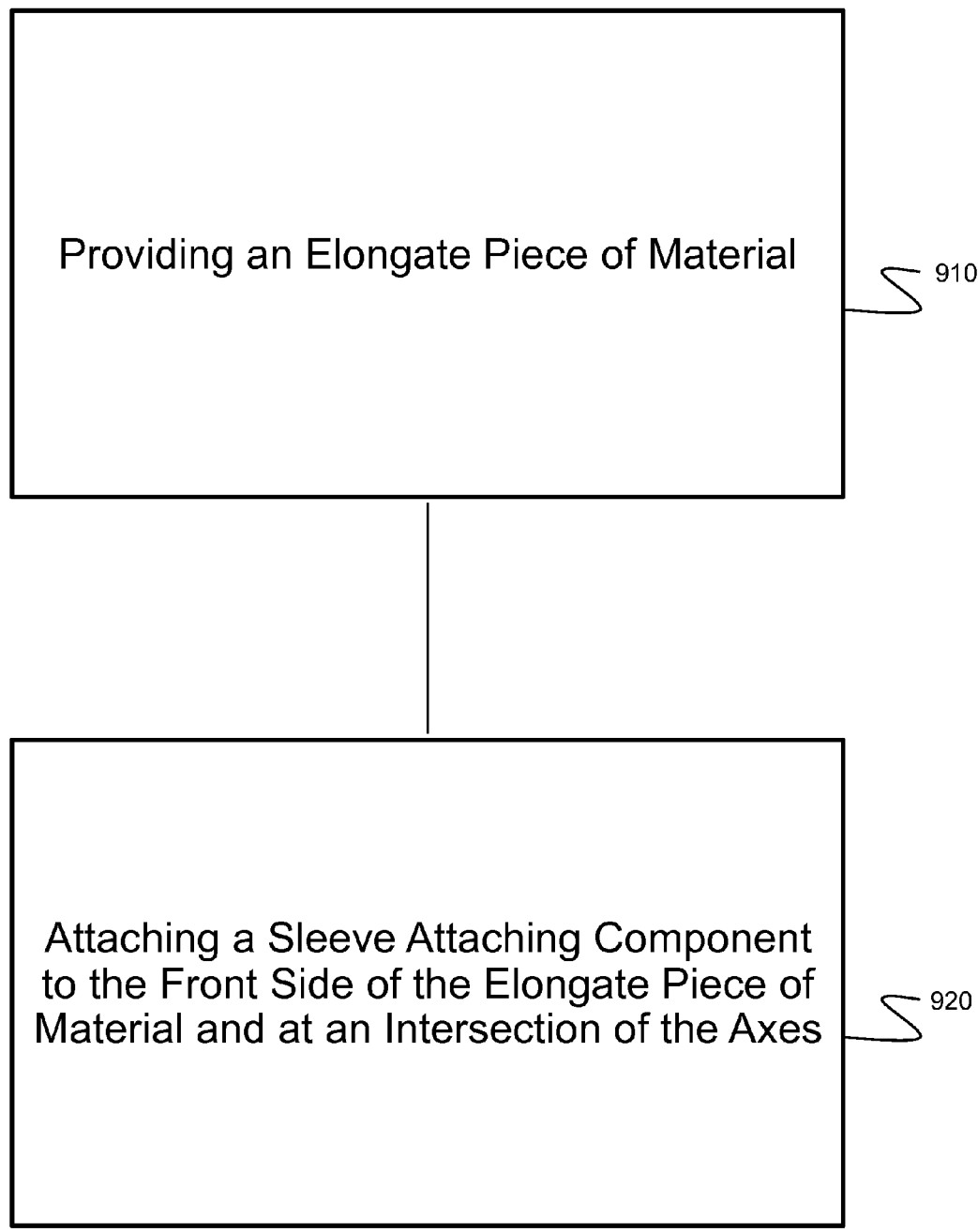
FIG. 9 is a flowchart of a method of providing a swaddle device according to an embodiment of the present disclosure.

Referring to FIG. 9, there is illustrated an exemplary method consistent with an embodiment of the present invention. The method 900 includes the following operations: providing an elongate piece of material having a front side, a back side that is opposite the front side, a vertical axis and a horizontal axis, the axes respectively bisecting the piece of material (operation 910); and attaching a sleeve attaching component to the front side of the elongate piece of material and at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of the infant (operation 920). The right and then the left wings are foldable over the chest of the infant and the fasteners cooperate to secure the folded wings in the folded condition.

The elongate piece of material may have (i) a right wing having a right fastener at a right end that is distal from the vertical axis, the right fastener part disposed along the horizontal axis and on the back side and (ii) a left fastener part at a left end that is distal from the vertical axis, the left fastener part disposed along the horizontal axis and on the front side.

As the foregoing illustrates, the applicant has discovered an innovative independent arm-security device and securing method, which can work in conjunction with virtually any existing swaddle blanket. Embodiments of the present invention may also be used as a standalone device to assist with administering medical care by restricting arm movement for either or both arms.

With arms secured in either the vertical or horizontal sleeve position, device is configured in such a way as to restrict elasticity and movement, either inward/outward or upward/downward. Also, arm can be secured, independent of one another, or together.

Each example provided herein is a non-limiting example. The various disclosed embodiments may be selectively combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A device for securing arms of an infant, comprising:
an elongate piece of material having a front side, a back side that is opposite the front side, a vertical axis and a horizontal axis, the axes respectively bisecting the piece of material;
a right wing having a right fastener at a right end that is distal from the vertical axis, the right fastener part disposed along the horizontal axis and on the back side;
a left wing having (i) a left fastener part at a left end that is distal from the vertical axis, the left fastener part disposed along the horizontal axis and on the front side; and
a sleeve attaching component attached on the front side of the elongate piece of material and located at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of the infant,
wherein, when at least one of the right and left sleeves retains a corresponding arm of the infant, the right and then the left wings are foldable over a chest or a front midsection of the infant and the fasteners cooperate to secure the folded wings in the folded condition.

2. The device of claim 1, wherein the sleeves are vertically oriented in disposed parallel with the vertical axis.

3. The device of claim 1, wherein the sleeves are horizontally oriented and disposed along the horizontal axis.

4. The device of claim 3, wherein the horizontally oriented sleeves retains at least one of the right and left arms of the infant in a horizontal position.

5. The device of claim 1, wherein the sleeve attachment component is permanently attached to the elongate material.

6. The device of claim 1, wherein the sleeve attaching component attaches to the front side of the elongate piece of material at the intersection of the axes behind the back of the infant.

7. A device for securing arms of an in6nt, comprising:
an elongate piece of material having a front side, a back side that is opposite the front side, a vertical axis and a horizontal axis, the axes respectively bisecting the piece of material;
a right wing having a right fastener at a right end that is distal from the vertical axis, the right fastener part disposed along the horizontal axis and on the front side;
a left wing having (i) a left fastener part near a left end that is distal from the vertical axis, the left fastener part disposed along the horizontal axis and on the back side; and
a sleeve attaching component attached on the front side of the elongate piece of material along the horizontal, the sleeve attaching component including a pair of sleeves disposed at least substantially on the right side of the vertical axis, the pair of sleeves including a right sleeve and a left sleeve, the sleeves disposed and configured to respectively retain right and left arms of the infant,
wherein, when at least one of the right and left sleeves retains a corresponding arm of the infant,
the left and then the right wings are foldable over a chest or a front midsection of the infant and the fasteners cooperate to secure the folded wings in the folded condition, and
the left wing is tuckable behind a back of the infant and between the back and the elongate material.

8. A method of securing arms of an infant, comprising:
providing an elongate piece of material having a front side, a back side that is opposite the front side, a vertical axis and a horizontal axis, the axes respectively bisecting the piece of material, the elongate piece of material having
(i) a right wing having a right fastener at a right end that is distal from the vertical axis, the right fastener part disposed along the horizontal axis and on the back side and
(ii) a left wing having a left fastener at a left end that is distal from the vertical axis, the left fastener part disposed along the horizontal axis and on the front side;
attaching a sleeve attaching component to the front side of the elongate piece of material and at an intersection of the axes, the sleeve attaching component including a pair of sleeves symmetrically disposed about the vertical axis, the pair of sleeves including a right sleeve and a left sleeve, the sleeves disposed and configured to respectively retain right and left arms of an infant,
wherein the right and then the left wings are foldable over a chest or a front midsection of the infant and the fasteners cooperate to secure the folded wings in the folded condition.

9. The method of claim 8, wherein, when sleeves are vertically oriented, the sleeves are disposed and configured to secure one or both of the arms and to dispose each secured arm slightly forward from sides of the infant towards a lap area of the infant.

10. The method of claim 8, wherein, when the sleeves are horizontally oriented, the sleeves are disposed and configured to one or both of the arms securely over a chest of the infant.

11. The method of claim 10, wherein the sleeves are disposed and configured to secure both of the arms in such a way as to cause the hands of the infant to overlap in a virtual touching position.

12. The method of claim 11, wherein the sleeves secure the arms in a still condition permitting minimal arm movement.

13. The method of claim 10, wherein, when the sleeves are horizontally oriented at least one of the right and left arms of the infant are oriented a long a horizontal plane.

14. The method of claim 8, wherein the sleeve attaching component attaches to the front side of the elongate piece of material at the intersection of the axes behind the back of the infant.

15. The device for securing arms of an infant according to claim 7, wherein the sleeve attaching component attaches to the front side of the elongate piece of material at the intersection of the axes behind the back of the infant.

16. The device for securing arms of an infant according to claim 7, wherein the sleeves are horizontally oriented and hold at least one of the right and left arms of the infant in a horizontal position.

* * * * *